(12) United States Patent
Seledtsov et al.

(10) Patent No.: US 10,695,408 B2
(45) Date of Patent: Jun. 30, 2020

(54) XENOGENIC NORMAL TISSUE-DERIVED VACCINES FOR BREAKING THE IMMUNE TOLERANCE TO TUMOR-ASSOCIATED, ANTIGENS

(71) Applicant: UAB "INNOVITA RESEARCH", Vilnius (LT)

(72) Inventors: Victor I. Seledtsov, Kaliningrad (RU); Galina V. Seledtsova, Novosibirsk (RU); Adas Darinskas, Vilnius (LT)

(73) Assignee: UAB "Innovita Research", Vilnius (LT)

( * ) Notice: Subject to any disclaimer, the term of this patent is extended or adjusted under 35 U.S.C. 154(b) by 302 days.

(21) Appl. No.: 15/514,100

(22) PCT Filed: Apr. 15, 2015

(86) PCT No.: PCT/IB2015/052738
§ 371 (c)(1),
(2) Date: Mar. 24, 2017

(87) PCT Pub. No.: WO2016/046651
PCT Pub. Date: Mar. 31, 2016

(65) Prior Publication Data
US 2017/0296642 A1    Oct. 19, 2017

(30) Foreign Application Priority Data
Sep. 26, 2014 (LT) ........................ 2014 112

(51) Int. Cl.
*A61K 39/00* (2006.01)
(52) U.S. Cl.
CPC .... *A61K 39/0011* (2013.01); *A61K 2039/515* (2013.01); *A61K 2039/70* (2013.01)
(58) Field of Classification Search
CPC ................................................. A61K 39/0011
USPC ....................................................... 424/277.1
See application file for complete search history.

(56) References Cited

FOREIGN PATENT DOCUMENTS

RU         2192884 C2    11/2002
WO    2007/106576 A2     9/2007

OTHER PUBLICATIONS

Gura (Science. 1997; 278: 1041-1042).*
Dennis (Nature. Aug. 7, 2006; 442: 739-741).*
Reagan-Shaw et al. (FASEB J, 2007, 22: 659-61).*
Byers, T. (CA Cancer Journal, 1999, 49: 353-361).*
Rees et al. (Nature, 1975, vol. 255, May 22, pp. 329-330).*
Zhang et al. (Asian Pacific J Cancer Prey, 2012, 13 (9), 4295-4300).*
Zhong, et al., "Induction of Antitumor Immunity Through Xenoplacental Immunization," Journal of Translational Medicine, vol. 4, No. 22, 2006, pp. 1-9.
Weber, et al., "Tumor Immunity and Autoimmunity Induced by Immunization with Homologous DNA," J. Clin. Invest., 1998, pp. 1258-1264.
Strioga, et al., "Xenogeneic Therapeutic Cancer Vaccines as Breakers of Immune Tolerance for Clinical Application: To Use or Not to Use?," Vaccine, vol. 32, 2014, pp. 4015-4024.
Seledtsov, et al., "Xenovaccinotherapy for Cancer," Intech, 2011, pp. 415-428.
Platzer, et al., "Antigen Cross-Presentation of Immune Complexes," Frontiers in Immunology, vol. 5, 2014, pp. 1-10.
Overwijk, et al., "gp100/pmel 17 is a Murine Tumor Rejection Antigen: Induction of "Self"-reactive, Tumoricidal T Cells Using High-Affinty, Altered Peptide Ligand," The Journal of Experimental Medicine, vol. 188, No. 2, 1998, pp. 277-286.
Lim, et al., "Cancer-Testis Antigens: The Current Status on Antigen Regulation and Potential Clinical Use," Am. J. Blood Res., vol. 2, No. 1, 2012, pp. 29-35.
Itoh, et al., "Recent Advances in Cancer Vaccines: An Overview," Jpn. J. Clin. Oncol., vol. 39, No. 2, 2009, pp. 73-80.
Khong, et al., Natural Selection of Tumor Variants in the Generation of "Tumor Escape" Phenotypes, Nat. Immunol., vol. 3, No. 11, 2002, pp. 999-1005.
Furbert-Harris, et al., "Inhibition of Prostate Cancer Cells Growth by Activated Eosinophils," The Prostate, vol. 57, 2003, pp. 165-175.
Fratta, et al., "The Biology of Cancer Testis Antigens: Putative Function, Regulation and Therapeutic Potential," Molecular Oncology, vol. 5, 2011, pp. 164-182.
Fernandez-Acenero, et al., "Prognostic Influence of Tumor-Associated Eosinophilic Infiltrate in Colorectal Carcinoma," Cancer, vol. 88, No. 7, 2000, pp. 1544-1548.
De Gruijl, et al., "Whole-Cell Cancer Vaccination: From Autologous to Allogeneic Tumor—and Dendritic Cell-Based Vaccines," Cancer Immunol Immunother, vol. 57, 2008, pp. 1569-1577.
Ambrose, et al., "Interruption of SV40 Oncogenesis with Human Foetal Antigen," Nature, vol. 233, No. 5316, 1971, pp. 194-195.
Brewer, et al., "Embryonic Vaccines Against Cancer: An Early History," Experimental and Molecular Pathology, vol. 86, 2009, pp. 192-197.
Andersen, et al., "Cancer Treatment: The Combination of Vaccination with Other Therapies," Cancer Immunol Immunother, vol. 57, 2008, pp. 1735-1743.
Rossi, et al., "Complete Protection Against Melanoma in Absence of Autoimmune Depigmentation After Rejection of Melanoma cells Expressing α(1,3)galactosyl Epitopes," Cancer Immunol Immunother, vol. 54, 2005, pp. 999-1009.
Parmiani, et al., "Autologous Versus Allogeneic Cell-Based Vaccines?," The Cancer Journal, vol. 17, No. 5, 2001, pp. 331-336.
International Search Report issued in Application No. PCT/IB2015/052738, dated Aug. 5, 2015.

* cited by examiner

*Primary Examiner* — Yan Xiao
(74) *Attorney, Agent, or Firm* — Young & Thompson

(57) ABSTRACT

Disclosed is an antitumor vaccine including testicular and fetal tissue-derived components. Cell preparations are prepared from normal tissues harvested directly from animals. Such vaccines may be used in the treatment and prevention of different cancers. For example, a vaccine consisting of glutaraldehyde-treated cells prepared from sheep testis and fetal lung has been found to be effective in inducing antitumor cell-mediated responses, as well as in prolonging the survival of mice with lung cancer.

5 Claims, 2 Drawing Sheets

Figure 1:
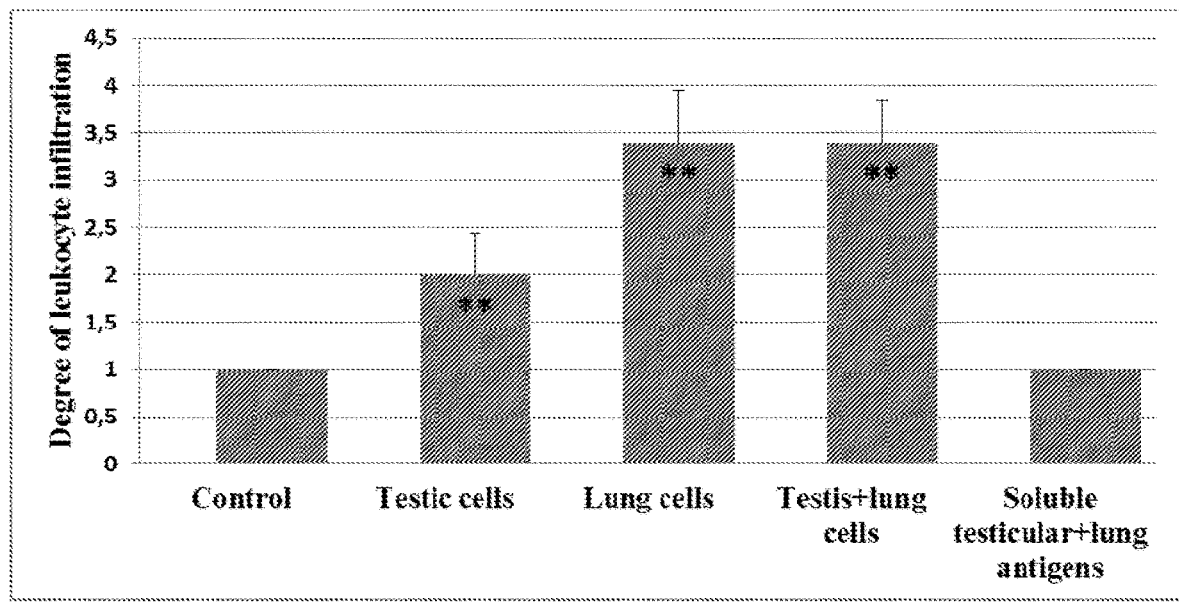

XENOGENIC NORMAL TISSUE-DERIVED VACCINES FOR BREAKING THE IMMUNE TOLERANCE TO TUMOR-ASSOCIATED, ANTIGENS

TECHNICAL FIELD

The present invention relates to xenogenic polyantigenic antitumor vaccines, and more specifically to vaccines comprising both common (shared) and tissue-specific, differentiation antigens derived from normal (non-tumor) tissues. The vaccines may be useful for cancer therapy and prevention.

BACKGROUND OF INVENTION

Up to date, a systemic treatment of cancer is based mainly on the use of chemotherapy. However, in the majority of cases, chemotherapy is not a radical treatment. In initially identified tumors there already exist cells that are resistant to toxic drug action, due to their biochemical properties. Furthermore, the proportion of such cells is progressively increased throughout the treatment period because they receive selective growth advantages over the cytotoxic drug-susceptible cells. It should also be noted that cytotoxic action of antineoplastic drugs is not selective: the drugs affect not only tumor, but also normal cells. Hence, there remains a need for the drugs with selective cytotoxic activity.

Tumor cells are distinguished from normal ones by quantitative and qualitative expression on their surfaces of potentially immunogenic structures (antigens). It is generally accepted that the immune responses induced by these structures can cause destruction of tumor cells, and that reactivity of the immune system can define the outcome of disease. All of the tumor-associated antigens (TAAs) can be divided into two groups: the first one involves the differentiation antigens that can be expressed not only in tumor, but also in normal cells, whereas the second one comprises of the products of mutated or viral genes, which can be expressed exclusively in malignant cells. The vast majority of TAAs belongs to the first group. Some of TAAs in this group, for example cancer/testis antigens (CTAs) can be expressed in a variety of tumors, due to commonality in the intracellular mechanisms involved in malignization of various types of cells. Other TAAs (for example oncofetal antigens) are defined by a type of a tumor and are mostly represented by tissue-specific differentiation antigens (reviewed by Strioga et al., 2014). In an adult organism CTAs are normally expressed only in immune privileged organs including as testis and placenta, and can be aberrantly expressed in cancer cells. For example, in the adult body the products of gene families MAGE, BAGE, GAGE and some others are mainly expressed in the testis rather than in other tissues and organs. On the other hand, many types of tumors may share expression of these CTAs (reviewed by Fratta et. al. 2011). CTAs possess a high immunogenic potential since they are "unknown" to the immune system and hence are not tolerated. Oncofetal antigens may be normally expressed at very low levels in normal tissues (for example alpha-fetoprotein in the liver) and can be overexpressed in some cancers or during various non-malignant pathologies. The overexpressed oncofetal antigens are less immunogenic than CTAs (Strioga et. al., 2014)

It should be noted that immunizations with one or several tumor-associated, antigenic peptides frequently fail to control overall tumor development, creating favorable conditions for growth of the tumor cell clones lacking vaccinal determinants. Moreover, due to a high lability of cancer genome, there is an antigenic diversity even in tumor cells of the same origin (reviewed by Khong H T, Restifo N P., 2002).

Since whole tumor cells express a variety of TAAs and are able to elicit a broad spectrum of immune responses, they could be more applicable to constructing cancer vaccines, compared to a single or just a few antigenic peptides. Moreover, antigenic cellular particles are usually much more immunogenic compared to soluble antigenic peptides, due to their ability to be wholly phagocytized by professional antigen-presenting cells capable of presenting identical, cell-derived peptides in association with major histocompatibility complex (MHC) molecules at a density sufficient to trigger T-cell responses.

Various types of tumor cell-based vaccines have been developed. Autological (made from the tumor cells of the same individual) and allogeneic (made from the tumor cells of a different individual of the same species) whole-cell vaccines, as well as vaccines on the basis of dendritic cells have been used for induction of specific antitumor immune responses (de Gruijl et. al., 2008; Itoh et. al., 2009). However, immunizations with unmodified homologous (autological or allogeneic) tumor cells have demonstrated only limited therapeutic success in cancer patients. There are two major reasons for the low immunogenicity of homologous cell vaccines. Firstly, as mentioned above, most of TAAs represent self-antigens, which are not inherently immunogenic. Secondly, antigen-presenting cells do not recognize the homologous tumor cells as potentially pathogenic targets that should be internalized and their antigens processed (Khong H T, Restifo N P., 2002). Accordingly, overcoming immune tolerance towards TAAs is a key task of cancer immunotherapy.

Certain approaches have been made to boost immunogenicity of autologic or allogeneic cancer vaccines, based on genetic modifications of vaccinal cells, rendering them superficially expressing costimulatory molecules and/or secreting immunostimulatory cytokines (de Gruijl et. al. 2008; Andersen et. al., 2008). However, all these kinds of modification are difficult to achieve in clinical practice as modification of tumor cells is technically complicated and time-consuming (reviewed by Parmiani et. al., 2011).

The use of xenogeneic TAAs has been suggested to overcome the immune tolerance to homological self TAAs. Indeed, many genes are highly evolutionarily conserved with various degrees of similarities among different species. Nevertheless, the small interspecific structural differences may confer increased immunogenicity to xenoproteins and provide a marked immune cross-reactivity directed against their homologous counterparts. In fact, xenoantigens may potentially represent an "altered self", with sufficient differences from self-antigens to render them immunogenic, but with sufficient similarities to allow reactive T cells to maintain recognition of self (reviewed by Seledtsov et. al., 2011; Strioga et. al., 2014). There is evidence that xeno-epitopes can bind host MHC molecules more strongly than epitopes derived from native homologous proteins, resulting in the formation of more sustained xenogeneic peptide/MHC complexes. Ultimately this leads to more potent xenoantigen-induced T cell responses, cross-reactive with self-protein-derived TAAs (Overwijk et. al., 1998).

The majority of studies concerning xenogenic vaccines have been carried out on animals with melanoma, the tumor that expresses a whole number of potentially immunogenic antigens. There is compelling evidence that xenogenic melanoma-associated antigens are much more effective in inducing antitumor immune responses in mice than are their murine analogs. For example, multiple immunizations of mice with human glycoproteins gp75 and gp-100 have been reported to be effective in preventing the growth of the syngeneic melanoma cells expressing the appropriate mouse analogs (Overwijk et. al., 1998; Weber et. al., 1998). Immunogenic and antitumor effects of xenovacination have been also reported in experimental models of hepatocellular carcinoma, glioma, neuroblastoma, colon cancer, and lung carcinoma. Theraupetic vaccinations were found to be capable of generating tumor-specific CD4+ and CD8+T lymphocytes, as well as antitumor antibodies (reviewed by Strioga et. al., 2014).

The data indicating the therapeutic potential of antitumor xenovaccination in humans are also accumulating. For example, a vaccine consisting of murine melanoma and carcinoma cells, as well as porcine testis cells has been reported to be immunologically and clinically effective in certain patients with melanoma and colorectal cancer (patent RU2192884C2). The published results suggest that xenogenic vaccines are safe to use, able to induce measurable cellular and humoral immune responses in patients, and may serve as effective means for treating melanoma, renal cancer, tumors of digestive system, lung cancer and prostate cancer (Seledtsov et. al., 2011).

It is important to note that all humans possess natural (preexisting) antibodies (Abs) that provide an acute rejection of any non-primate cells and function as a major barrier for transplantation of animal organs in humans. A significant part of these Abs represents IgG specific to the alpha-gal epitope that is abundantly expressed on glycoproteins and glycolipids of nonprimate mammals and NewWorld monkeys (Galili U., 1993) By opsonization of xenogenic cells, the natural Abs promote internalization of antigenic material in antigen-presenting cells APC via a Fcg-receptor-mediated mechanism, and enhance greatly the immunogenic cross-presentation of antigenic peptides to antigen-specific CD4+ and CD8+T lymphocytes (Galili U., 1993; Platzer et. al., 2014). This proposition is consistent with the published results showing that rejection of alpha-Gal positive tumor cells can efficiently boost the immune response to other tumor-associated antigens present in alpha-Gal negative tumor cells (Rossi et. al., 2005).

The xenogenic cell-based vaccines are typically presented in the form of whole tumor cells or their lysates (Seledtsov et. al., 2011). However, using tumor cell cultures is rather expensive and they are not always reproducible sources of TAAs. It is also important to know that although the tumor cells used in the xenogenic vaccines are not vital, such vaccines may still contain components that could be involved in tumorogenesis.

As already mentioned, the vast majority of TAAs belongs to the differentiation antigens that are highly expressed in normal cells involved in organ morphogenesis. This raises the possibility of obtaining xenogenic vaccinal antigens from normal tissues where they are highly expressed. For example, cancer/testis antigens (CTAs) pertaining to so-called common TAAs can be readily obtained from normal testicular tissues and could be subsequently used as universal antitumor immunogens. According to published data (reviewed Lim et. al. 2012), immune responses directed against CTAs may cause tumor destruction, while not damaging normal tissues and organs. Normal fetal-derived tissues can be suitable sources for vaccinal oncofetal antigens. Placenta is also well known to express a whole range of differentiation antigens, including those shared by different tumors including melanoma (Zhong et al, 2006).

Despite the above said, there remains a need for a cancer vaccine, which would be clinically effective, easily prepared, reproducible and inexpensive. It is also highly desirable that a cancer vaccine-based technology could be applicable for treatment or prevention of more than one type of cancer or its specificity could be easily changed. Xenogenic normal tissue-derived vaccines may conceivably meet all these requirements.

SHORT DESCRIPTION OF DRAWINGS

FIG. 1. Shows leukocyte infiltration of a tumor in the control and vaccinated mice, where "**" marks P<0.05 compared to the control in this and other figures.

Figure 2:
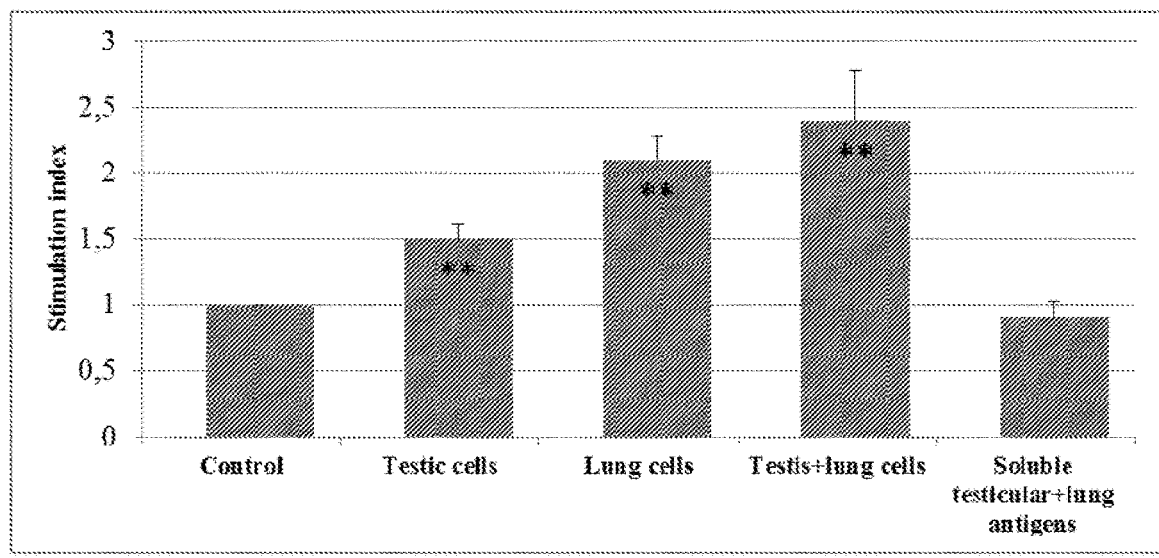

FIG. 2. Shows LLC antigen-induced production of IL-2 by the spleen cells isolated from the control and vaccinated mice.

Figure 3:
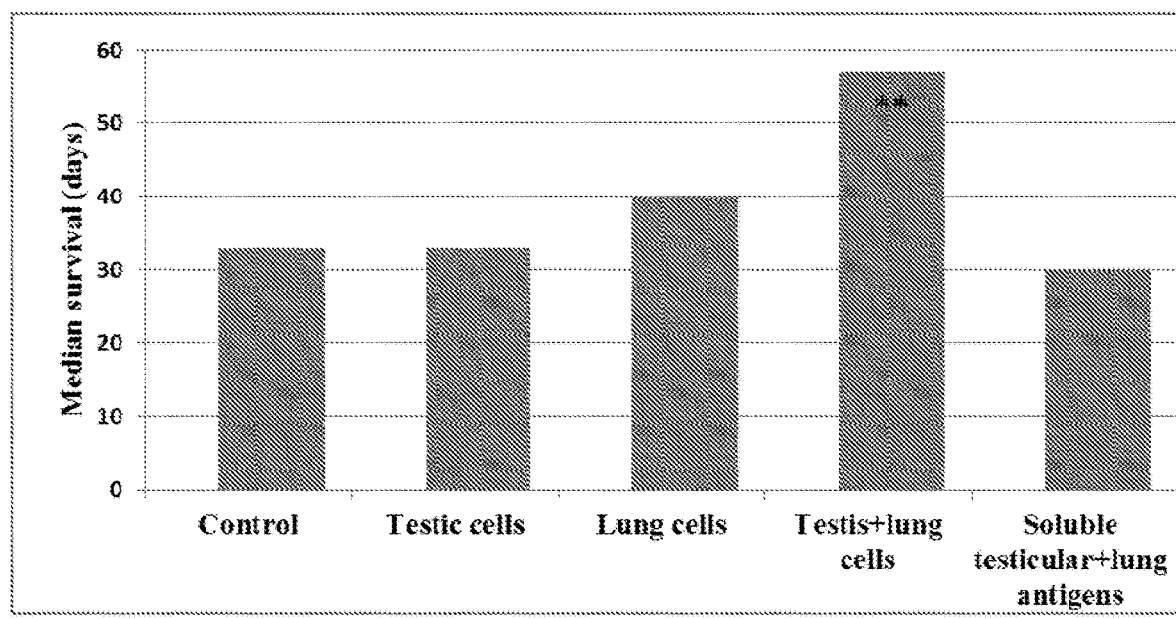

FIG. 3. Shows the median survival of the control and vaccinated mice.

DESCRIPTION OF THE INVENTION

The present invention is directed to overcoming the preexisting immune tolerance to tumor-associated, differentiation antigens. A xenogeneic vaccine is provided that comprises components derived from normal tissue harvested from one species of a mammal to prevent or treat tumors in a mammal of another species. The objects of this invention are vaccine compositions comprising xenogenic testicular cells and xenogenic tissue-derived cells. It is suggested that such vaccine compositions can be useful for treating numerous cancers and have apparent advantages over all previously described vaccines. They are much more immunogenic compared to autological or allogeneic analogs. They induce polyclonal immune responses and therefore are more effective in tumor growth inhibition in comparison with peptide-based vaccines capable of inducing only oligoclonal immune reactions.

Very important advantage of the xenogenic normal tissue-derived vaccines of the invention is the use of unlimited and reproducible sources for their manufacturing. Numerous amounts of testicular and tissue-derived cells can be obtained from a chosen mammal source. Preferably, said mammal is sheep, pig, cat or mouse. Most preferred animal source is a sheep.

The vaccine compositions will usually comprise testicular and fetal tissue-derived cells from the same xenogenic species; however, in some embodiments, testicular cells from a first xenogenic species and tissue-derived cells from a second xenogenic species may be used, for example testicular cells from a sheep and tissue-derived cells from a pig, or vice-versa.

The amounts of the components of the vaccine composition will be apparent to the skilled person. The preferred ratio of testicular and tissue-derived cells in the vaccine composition is from 1:10 to 10:1; more preferred ratio is from 1:5 to 5:1; most preferred ratio is 1:1.

The current invention provides a possibility to manufacture a number of vaccines useful for treating different cancer types. Each specialized vaccine is achieved by a combination of common (shared) and tissue-specific TAAs. For example, a vaccine composition for lung cancer may comprise testicular cells and lung tissue-derived cells; a vaccine composition for renal cancer may consist of testicular cells and fetal renal tissue-derived cells; and so on. The vaccine composition for lung cancer is preferred. It should be noted that animal fetal tissues can be sources of not only tissue-specific, both also common differentiation antigens.

In some embodiments, the said vaccine composition is described as a heterologous mixture of antigens presented by whole tissue cells that were processed with glutaraldehyde. Other substances can be used for fixation and preservation of the cells, such as formaldehyde and alcohol. Vaccines may be also used in the form of intact or lyophilized cell lysates.

The present invention provides a pharmaceutical composition comprising a therapeutically effective amount of xenogenic testicular cells and xenogenic fetal tissue-derived cells. The pharmaceutical compositions may be for human or animal usage in human and veterinary medicine.

EXAMPLES

Materials and Methods
Mice.

C57BL/6 (B6; H-$2^b$) mice were bred in our own facilities. The mice were male and of ages ranging between 4 and 6 months. They received autoclaved food and boiled water.
Tumor Cell Line.

LLC carcinoma cell line of B6 (H-$2^b$) origin has been obtained from Moscow Oncologic Scientific Center of Russian Academy of Medical Sciences and was maintained in RPMI 1640 medium supplemented with 10% FCS, 2 mM 1-glutamine, and antibiotics.
Preparation of the Tumor Cell Lysate for Immunoreactivity Assay.

LLC cells were harvested, washed extensively with phosphate-buffered saline (PBS) and further stored at −20° C. until use.
Preparation of Vaccinal Components.

Testis were isolated from the adult sheep. After being released from its capsules, the spermatogenous tissue was fragmented with scissors and then suspended with the aid of a glass homogenizer using gentle pressing of tissue fragments in the cold PBS. The cell suspension was stayed for 7 min to sediment large aggregates. After being transferred from the homogenizer into a tube, the cells were washed with the cold PBS. Next, a portion of the cells was incubated in 0.1% glutaraldehyde (v/v) at 37° C. for 20 minutes and then extensively washed to produce a vaccinal cell preparation. Another cell portion underwent a procedure of freezing and thawing three times and was then centrifuged to obtain the supernatant containing soluble testicular antigens.

The lungs were isolated from the sheep fetuses at 3 to 4 months of age. The isolated lungs were extensively washed within a large volume of cold PBS and then fragmented with scissors. The cells were gently squeezed out from the lung fragments into the cold PBS and transferred into a tube. The vaccinal glutaraldehyde-treated lung cells and the supernatant containing soluble lung antigens were prepared essentially as described above.
Tumor Implantation and Vaccination Procedures.

Five groups of B6 male mice, each of which consisted of 15 animals, were established. All mice were injected with LLC cells ($2 \times 10^5$/mouse) subcutaneously (s.c.) on day 0.
1. The control group. The mice did not undergo any immunization.
2. The group vaccinated with xenogenic testis cells. The mice were subcutaneously immunized with glutaraldehyde-treated testis cells on day 3, 7, and 11 at a dose of $2 \times 10^6$, $4 \times 10^6$, and $6 \times 10^6$/mouse, respectively.
3. The group vaccinated with xenogenic lung cells. The mice were immunized with glutaraldehyde-treated lung cells on day 3, 7, and 11 at a dose of $2 \times 10^6$, $4 \times 10^6$, and $6 \times 10^6$/mouse, respectively.
4. The group vaccinated with xenogenic testis and lung cells. The mice received immunizations with glutaraldehyde-treated testis and lung cells at a dose of $1 \times 10^6$, $2 \times 10^6$, and $3 \times 10^6$/mouse for each kind of cells on day 3, 7, and 11, respectively.
5. The group vaccinated with xenogenic soluble testicular and lung antigens. The mice were immunized thrice with a mixture of soluble testis and lung products at the amounts equivalent the vaccinal cells used in the fourth group.
Immunoreactivity Analysis.

Five mice from each group were analysed for immunoreactivity to LLC carcinoma antigens at day 18 after tumor implantation. For histological examinations, the microscopic sections of a thickness of 5-to-7 µm were stained with a hematoxylin-eosin. The degree of leukocyte infiltration was scored from 0 to 5. For T-cell reactivity assay, the spleens were suspended with the aid of a glass homogenizer. The cell suspensions were stayed for 7 min to seat down large aggregates and the single-cell suspensions were then transferred from the homogenizer into a tube. After being extensively washed with the cold medium, spleen cells were cultured at $2 \times 10^5$/well with lysates of LLC cells (each $5 \times 10^4$/well), or without them in control, in a 96-well round-bottom plate in serum-free medium for 3 days. Amounts of interleukin-2 (IL-2) in the cultural supernatants were assessed using commercially available enzyme-linked immunosorbent assays (ELISA). Stimulation index was calculated as follows: test IL-2 level/control IL-2 level.
Survival Registration.

Mice were observed daily for survival and dead animals were autopsied. Evidence of tumors was grossly detected with clearly visible metastasis process.
Statistics.

The statistical significance of the data was determined using the Student's test. A P-value of <0.05 was considered to be statistically significant. The Kaplane-Meier method was employed to estimate overall survival.

Example 1

Vaccinations with Xenogenic Tissue-Derived Cells Stimulate Infiltration of the Tumor with Leukocytes The inflammatory response at the tumor margin was evaluated by enumerating mononuclear and granulocytic cells over ten high-powered (40× objective) fields. As can be seen in FIG. 1, xenovaccinations of tumor-bearing mice with either testis or lung cells, as well as a mixture of those cells induced a marked leukocyte infiltration of the tumor, whereas vaccinations with soluble xenogenic antigens have no such an effect. The detected inflammatory responses were composed of eosinophils (nearly 20%), neutrophils (40%), lymphocytes (30%) and macrophages (10%). The marked tumor-associated tissue eosinophilia at the tumor margins of cell-vaccinated mice distinguishes those inflammatory responses from that observed in the tumors of control mice. A tumor-associated eosinophilic infiltrate has been shown to be a favorable prognostic indicator in colorectal carcinoma and early esophageal squamous cell carcinoma (FemandeZ-Acemo, et. al., 2000; OhashiY et. al. 2000). Activated eosinophils or their culture supernatants were found to be capable of inhibiting significantly the growth of the cultured human prostate cancer cells (Furber't-Harris et. al., 2003). A possible role for eosinophils in the protective immune response conferred by cell-based xenovaccination could exist in our own experiments.

Example 2

Vaccinations with Xenogenic Tissue-Derived Cells Induce Immune Reactivity to Tumor Cells.

The present example demonstrates that immunization with xenogenic tissue-derived cells is able to induce antitumor T-reactivity evidenced by producing interleukin-2 (IL-2). IL-2 is well known to be a pivotal mediator in the mechanism of generating the long-lasting adaptive immunity. As shown in FIG. 2, soluble xenogenic (testicular plus lung) antigens failed to induce T-cell reactivity to LLC antigens in tumor-bearing mice. Adjuvants appear to be required to render xenogenic soluble antigens capable of inducing immune responses with a notable efficiency. In contrast to the soluble antigens, both testis and lung cells were able to induce detectable antitumor reactivity ($p<0.05$ compared to control). Noteworthy that the combined vaccinations with testis and lung cells were more effective in this regard compared to vaccinations with either testis cells or lung cells alone.

Example 3

Vaccinations with Xenogenic Tissue-Derived Cells Prolong Survival of Tumor-Bearing Mice.

As can be seen in FIG. 3, the median survival in LLC-bearing —bearing mice vaccinated with a combination of xenogenic testis and lung cells was significantly longer ($P<0.05$) than was the control LLC-bearing mice. The vaccinations with either testis cells or lung cells alone barely slightly prolong the survival LLC-bearing mice. Xenogenic soluble antigens were ineffective in this regard. From these data it may be concluded that 1) in the absence of immunoadjuvants the xenogenic tissue-derived cells are much more effective as a cancer vaccine, than are xenogenic soluble antigens of the same origin; and 2) antitumor clinical responses may be largely potentiated by combining vaccinal cells, expressing common (for example testicular) and fetal tissue-specific (for example fetal lung) antigens which may express in tumor cells.

REFERENCES

1. Strioga M. M., Darinskas A., Pasukoniene V. et. al. Vaccine. 2014; 32:4015-4024.
2. Fratta E., Coral S., Covre A. et. al. Mol Oncol. 2011; 5:164-82.
53. Khong H. T., Restifo N. P. Nat Immunol 2002; 3: 999-1005.
4. de Gruijl T. D., van den Eertwegh A. J., Pinedo H. M., Scheper R. J. Cancer Immunol Immunother. 2008; 57:1569-77.
5. Itoh K., Yamada A., Mine T., Noguchi M. Jpn J Clin Oncol 2009; 39: 73-80.
6. Parmiani G, Pilla L., Maccalli C., Russo V. Cancer J. 2011; 17:331-336.
7. Andersen M. H., Smrensen R. B., Schrama D., et al. Cancer Immunol Immunother 2008; 57: 1735-43.
8. Seledtsov V. I., Shishkov A. A, Seledtsova G V. In:Ozdemir O, editor. Current cancer treatment—novel beyond conventionalapproaches. InTech. 2011; 415-428.
9. Overwijk W. W., Tsung A., Irvine K. R. et. al. J Exp Med. 1998; 188:277-286.
10. Weber L. W., Bowne W. B., Wolchok J. D. et al. J Clin Invest. 1998; 102):1258-1264.
11. Galili U. Immunol Today 1993; 14:480-482.
12. Platzer B., Stout M., Fiebiger E. Front Immunol. 2014; 5:140.
13. Rossi G. R., Unfer R. C., Seregina T., Link C. J. Cancer Immunol Immunother. 2005; 54: 999-1009.
14. Lim S. H., Zhang Y., Zhang J. Am J Blood Res. 2012; 2:29-35.
15. Zhong Z., Kusznieruk K. P., Popov I. A. et. al., J Transl Med. 2006; 4:22.
16. Fernandez-Acerno M. J., et al. Cancer 2000; 88: 1544-48.
17. Ohashi Y., et al. Anticancer Res. 2000; 20: 3025-30.
18. Furbert-Harris P. et al. Prostate 2003; 57:165-175.

The invention claimed is:

1. A composition comprising xenogenic adult derived cells and xenogenic fetal tissue-derived cells for use in the treatment of a lung tumor in a subject, wherein the composition comprises adult testis-derived and fetal lung tissue-derived cells.

2. A composition according to claim 1, wherein fixed whole cells are used.

3. A composition according to claim 2, wherein the cells are fixed with glutaraldehyde.

4. A composition according to claim 1, wherein intact cell lysates are used.

5. A composition according to claim 1, wherein lyophilized cell lysates are used.

* * * * *